US011123094B2

(12) United States Patent
Ross et al.

(10) Patent No.: US 11,123,094 B2
(45) Date of Patent: Sep. 21, 2021

(54) ULTRASONIC SURGICAL INSTRUMENTS AND METHODS FOR SEALING AND/OR CUTTING TISSUE

(71) Applicant: Covidien LP, Mansfield, MA (US)

(72) Inventors: Anthony B. Ross, Boulder, CO (US); David J. Van Tol, Boulder, CO (US)

(73) Assignee: Covidien LP, Mansfield, MA (US)

(*) Notice: Subject to any disclaimer, the term of this patent is extended or adjusted under 35 U.S.C. 154(b) by 417 days.

(21) Appl. No.: 16/200,808

(22) Filed: Nov. 27, 2018

(65) Prior Publication Data

US 2019/0175208 A1 Jun. 13, 2019

Related U.S. Application Data

(60) Provisional application No. 62/598,035, filed on Dec. 13, 2017.

(51) Int. Cl.
*A61B 17/32* (2006.01)
*A61B 17/295* (2006.01)
(Continued)

(52) U.S. Cl.
CPC .... *A61B 17/320092* (2013.01); *A61B 17/295* (2013.01); *A61B 2017/0003* (2013.01);
(Continued)

(58) Field of Classification Search
CPC .......... A61B 17/295; A61B 17/320092; A61B 2017/320095; A61B 2090/064;
(Continued)

(56) References Cited

U.S. PATENT DOCUMENTS

D223,367 S 4/1972 Kountz
3,794,236 A 2/1974 Salzer et al.
(Continued)

FOREIGN PATENT DOCUMENTS

CN 1103807 C 3/2003
DE 390937 C 3/1924
(Continued)

OTHER PUBLICATIONS

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
(Continued)

*Primary Examiner* — Phong Son H Dang
(74) *Attorney, Agent, or Firm* — Carter, DeLuca & Farrell LLP (57) ABSTRACT

An ultrasonic surgical system includes an ultrasonic generator configured to output a drive signal, an ultrasonic transducer configured to receive the drive signal and output mechanical motion, a waveguide configured to transmit the mechanical motion to a blade disposed at a distal end portion thereof, a sensor, and a controller. The blade is configured to oscillate in response to receipt of the mechanical motion and defines a displacement when oscillating. The sensor is configured to sense a property indicative of tension on tissue and the controller is configured to adjust the drive signal to thereby adjust the displacement based upon the sensed property. A method of treating tissue includes applying a drive signal to an ultrasonic transducer to oscillate an ultrasonic blade, sensing a property indicative of a tension on the tissue, and adjusting the drive signal based upon the sensed property to thereby adjust the displacement of the blade.

20 Claims, 6 Drawing Sheets

(51) Int. Cl.
  *A61B 17/00* (2006.01)
  *A61B 90/00* (2016.01)
(52) U.S. Cl.
  CPC ........... *A61B 2017/00026* (2013.01); *A61B 2017/320075* (2017.08); *A61B 2017/320094* (2017.08); *A61B 2017/320095* (2017.08); *A61B 2090/064* (2016.02)
(58) Field of Classification Search
  CPC ......... A61B 2017/320075; A61B 2017/00026; A61B 2017/0003; A61B 2017/320094
  See application file for complete search history.

(56) References Cited

U.S. PATENT DOCUMENTS

| | | |
|---|---|---|
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,190,517 A | 3/1993 | Zieve et al. |
| D354,218 S | 1/1995 | Van de Peer |
| 5,449,370 A | 9/1995 | Vaitekunas |
| 5,733,281 A | 3/1998 | Nardella |
| 5,873,873 A | 2/1999 | Smith et al. |
| 5,947,984 A | 9/1999 | Whipple |
| 5,980,510 A | 11/1999 | Tsonton et al. |
| 6,004,335 A | 12/1999 | Vaitekunas et al. |
| D424,693 S | 5/2000 | Pruter |
| D424,694 S | 5/2000 | Tetzlaff et al. |
| D425,201 S | 5/2000 | Tetzlaff et al. |
| 6,063,098 A | 5/2000 | Houser et al. |
| 6,068,647 A | 5/2000 | Witt et al. |
| D449,886 S | 10/2001 | Tetzlaff et al. |
| 6,352,532 B1 | 3/2002 | Kramer et al. |
| D457,958 S | 5/2002 | Dycus et al. |
| D457,959 S | 5/2002 | Tetzlaff et al. |
| 6,454,781 B1 | 9/2002 | Witt et al. |
| 6,458,142 B1 | 10/2002 | Faller et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| 7,108,695 B2 | 9/2006 | Witt et al. |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,058,771 B2 | 11/2011 | Giordano et al. |
| 8,253,303 B2 | 8/2012 | Giordano et al. |
| 8,512,365 B2 | 8/2013 | Wiener et al. |
| 8,535,340 B2 | 9/2013 | Allen |
| 8,779,648 B2 | 7/2014 | Giordano et al. |
| 9,017,326 B2 | 4/2015 | DiNardo et al. |
| 9,314,261 B2* | 4/2016 | Bales, Jr. .......... B06B 1/0223 |
| 9,445,832 B2 | 9/2016 | Wiener et al. |
| 10,251,664 B2* | 4/2019 | Shelton, IV .......... H01M 50/20 |
| 2002/0183774 A1 | 12/2002 | Witt et al. |
| 2006/0079875 A1 | 4/2006 | Faller et al. |
| 2006/0079877 A1 | 4/2006 | Houser et al. |
| 2007/0282333 A1 | 12/2007 | Fortson et al. |
| 2007/0282334 A1 | 12/2007 | Young et al. |
| 2008/0097501 A1 | 4/2008 | Blier |
| 2008/0319374 A1 | 12/2008 | Zacharias |
| 2009/0036914 A1 | 2/2009 | Houser |
| 2009/0223033 A1 | 9/2009 | Houser |
| 2011/0082486 A1 | 4/2011 | Messerly et al. |
| 2012/0116391 A1* | 5/2012 | Houser .................. A61B 34/76 606/41 |
| 2013/0253480 A1* | 9/2013 | Kimball ......... A61B 17/320092 606/1 |
| 2013/0267975 A1* | 10/2013 | Timm ............ A61B 17/320092 606/169 |
| 2014/0018668 A1* | 1/2014 | Zheng ..................... A61B 8/488 600/424 |
| 2015/0157354 A1* | 6/2015 | Bales, Jr. .............. B06B 1/0223 606/169 |
| 2017/0105751 A1* | 4/2017 | Hibner ........... A61B 17/320092 |
| 2017/0164973 A1* | 6/2017 | Lesko ................ A61B 18/1206 |
| 2017/0172606 A1* | 6/2017 | Riestenberg ... A61B 17/320068 |
| 2017/0202570 A1* | 7/2017 | Shelton, IV ... A61B 17/320092 |
| 2017/0202591 A1* | 7/2017 | Shelton, IV .......... A61B 18/00 |
| 2017/0202609 A1* | 7/2017 | Shelton, IV ....... A61B 18/1445 |
| 2018/0049817 A1* | 2/2018 | Swayze ............. A61B 18/1445 |
| 2020/0390488 A1* | 12/2020 | Stamm ............. A61B 17/00234 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238125 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 3/2003 |
| EP | 1820460 A2 | 8/2007 |
| EP | 2314235 A2 | 4/2011 |
| FR | 179 607 | 11/1906 |
| FR | 1275415 A | 11/1961 |
| FR | 1347865 A | 1/1964 |
| FR | 2 235 669 A1 | 1/1975 |

(56) References Cited

FOREIGN PATENT DOCUMENTS

| | | |
|---|---|---|
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2 862 813 A1 | 5/2005 |
| FR | 2 864 439 A1 | 7/2005 |
| JP | 55106 | 1/1993 |
| JP | 0540112 A | 2/1993 |
| JP | 06343644 | 12/1994 |
| JP | 07265328 | 10/1995 |
| JP | 08056955 | 3/1996 |
| JP | 08252263 A | 10/1996 |
| JP | 09000492 A | 1/1997 |
| JP | 09010223 | 1/1997 |
| JP | 11244298 | 9/1999 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 2010035831 A1 | 4/2010 |
| WO | 2016032724 A1 | 3/2016 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology. vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions", In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone", Neurosurgery 15: (1984) pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts". Nov. 1, 2003; 4 pages.
Geddes et al.. "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Jarrett et al., "Use of the LigaSure.TM. Vessel Sealing System for Peri-Hilar Vessels in Laparoscopic Nephrectomy" Sales/Product Literature 2000.
Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole, M.D., et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al. "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page; Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot. Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).

P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001 pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.-Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.

(56) References Cited

OTHER PUBLICATIONS

Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
First Examination Report issued in corresponding European Application No. 18211840.6 dated Oct. 2, 2020, 5 pages.
Extended European Search Report issued in corresponding European Application No. 18211840.6 dated Apr. 8, 2019, 7 pages.

* cited by examiner

ULTRASONIC SURGICAL INSTRUMENTS AND METHODS FOR SEALING AND/OR CUTTING TISSUE

CROSS REFERENCE TO RELATED APPLICATION

The present application claims the benefit of and priority to U.S. Provisional Application Ser. No. 62/598,035, filed on Dec. 13, 2017 the entire contents of which are incorporated herein by reference.

BACKGROUND

Technical Field

The present disclosure relates to ultrasonic surgical instruments and, more particularly, to ultrasonic surgical instruments and methods for sealing and/or cutting tissue.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to seal and/or cut tissue.

Typically, an ultrasonic surgical instrument is configured to transmit ultrasonic energy produced by a generator and transducer assembly along a waveguide to an end effector that is spaced-apart from the generator and transducer assembly. The end effector, in turn, is configured to transmit the ultrasonic energy to tissue to treat the tissue, e.g., to seal and/or cut tissue. With respect to cordless ultrasonic instruments, for example, a portable power source, e.g., a battery, and the generator and transducer assembly are mounted on the handheld instrument itself, while the waveguide interconnects the generator and transducer assembly and the end effector. Corded ultrasonic instruments operate in similar fashion except that, rather than having the generator and power source mounted on the handheld instrument itself, the handheld instrument is configured to connect to a standalone power supply and/or generator via a corded connection.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an ultrasonic surgical system is provided including an ultrasonic generator configured to output a drive signal, an ultrasonic transducer coupled to the ultrasonic generator and configured to receive the drive signal and output mechanical motion in response thereto, a waveguide coupled to the ultrasonic transducer and configured to transmit the mechanical motion therealong, a blade disposed at a distal end portion of the waveguide, a sensor, and a controller. The blade is configured to oscillate in response to receipt of the mechanical motion from the waveguide. The blade defines a displacement when oscillating. The sensor is configured to sense a property indicative of tension on tissue. The controller is configured to adjust the drive signal to thereby adjust the displacement based upon the sensed property.

In an aspect of the present disclosure, the sensor is configured to sense a force on the waveguide. Alternatively or additionally, the sensor is configured to sense an impedance of the ultrasonic transducer.

In another aspect of the present disclosure, if the sensed property indicates tension on tissue is increased above a threshold, the controller is configured to adjust the drive signal to increase the displacement of the blade. Alternatively or additionally, if the sensed property indicates tension on tissue is decreased below a threshold, the controller is configured to adjust the drive signal to decrease the displacement of the blade.

In another aspect of the present disclosure, an activation switch is operably coupled to the ultrasonic generator and selectively activatable in a "CUT" mode and a "SEAL" mode.

In still another aspect of the present disclosure, when the activation switch is activated in the "SEAL" mode, if the sensed property indicates tension on tissue is increased, the controller is configured to adjust the drive signal to decrease the displacement of the blade.

In yet another aspect of the present disclosure, when the activation switch is activated in the "CUT" mode, if the sensed property indicates tension on tissue is increased, the controller is configured to adjust the drive signal to increase the displacement of the blade.

In still yet another aspect of the present disclosure, a handle assembly supports the ultrasonic transducer thereon and the waveguide extends distally from the handle assembly. In such aspects, the handle assembly may further support the ultrasonic generator and a battery assembly, configured to power the ultrasonic generator to produce the drive signal, thereon.

In another aspect of the present disclosure, the controller is configured to control an amount of power delivered from the battery assembly to the ultrasonic generator to thereby adjust the drive signal.

A method of treating tissue provided in accordance with aspects of the present disclosure includes applying a drive signal to an ultrasonic transducer to oscillate an ultrasonic blade adjacent tissue, sensing a property indicative of a tension on the tissue, and adjusting the drive signal applied to the ultrasonic transducer based upon the sensed property to thereby adjust a displacement of the blade.

In an aspect of the present disclosure, sensing the property includes sensing a force on a waveguide coupled to the ultrasonic blade. Alternatively or additionally, sensing the property includes sensing an impedance of the ultrasonic transducer.

In another aspect of the present disclosure, if the sensed property indicates tension on tissue is increased above a threshold, the drive signal is adjusted to increase the displacement of the blade. Alternatively or additionally, if the sensed property indicates tension on tissue is decreased below a threshold, the drive signal is adjusted to decrease the displacement of the blade.

In still another aspect of the present disclosure, the method further includes determining whether a "CUT" mode of operation or a "SEAL" mode of operation is selected and adjusting the drive signal applied to the ultrasonic transducer based upon the sensed property and the selected mode of operation to thereby adjust the displacement.

In yet another aspect of the present disclosure, in the "SEAL" mode of operation, if the sensed property indicates tension on tissue is increased, the drive signal is adjusted to decrease the displacement of the blade. Additionally or alternatively, in the "CUT" mode, if the sensed property indicates tension on tissue is increased, the drive signal is adjusted to increase the displacement of the blade.

In still yet another aspect of the present disclosure, adjusting the drive signal includes adjusting an amount of power delivered from a power source to an ultrasonic generator configured to output the drive signal.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1:
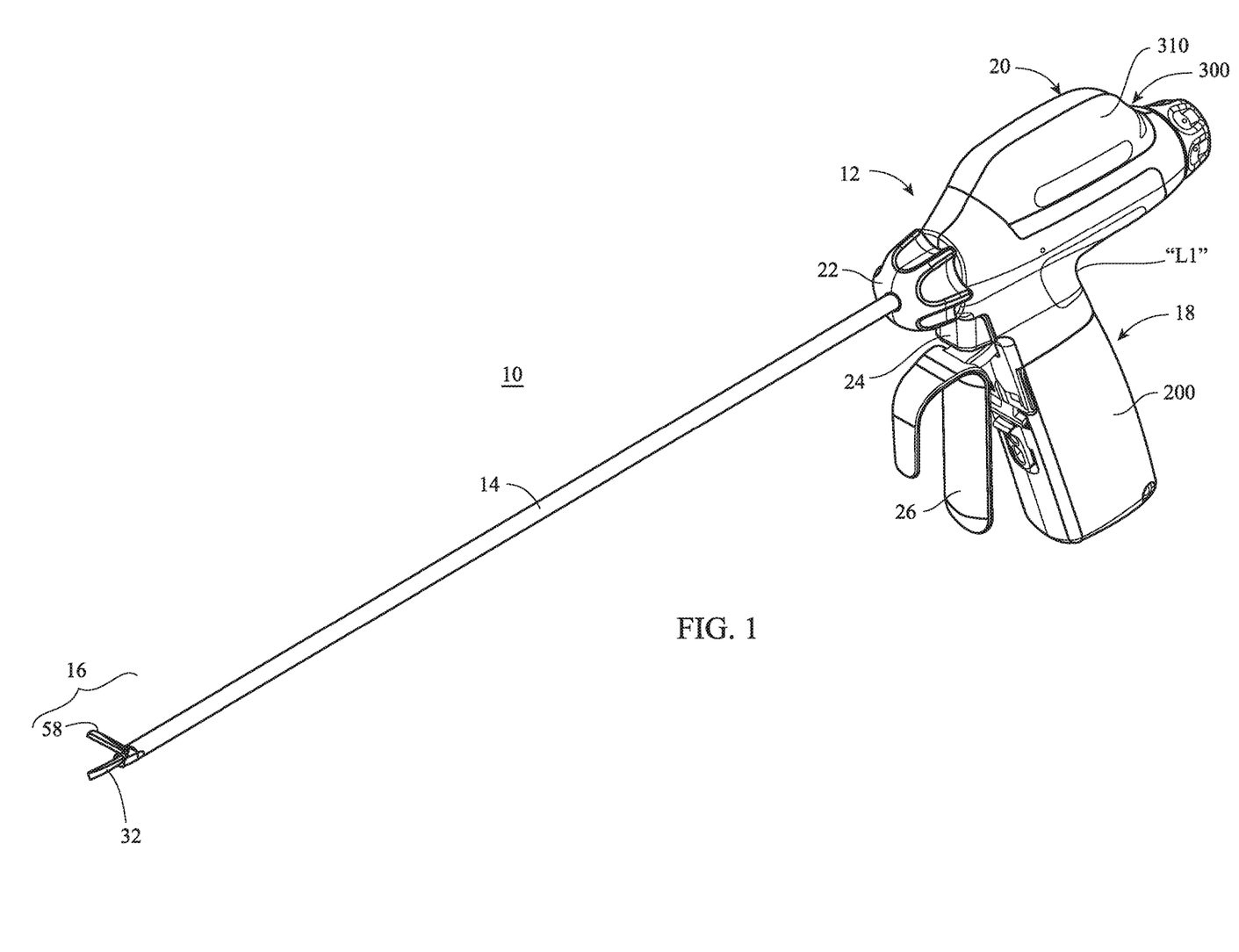
FIG. 1 is a side, perspective view of an ultrasonic surgical instrument provided in accordance with aspects of the present disclosure.
Figure 2:
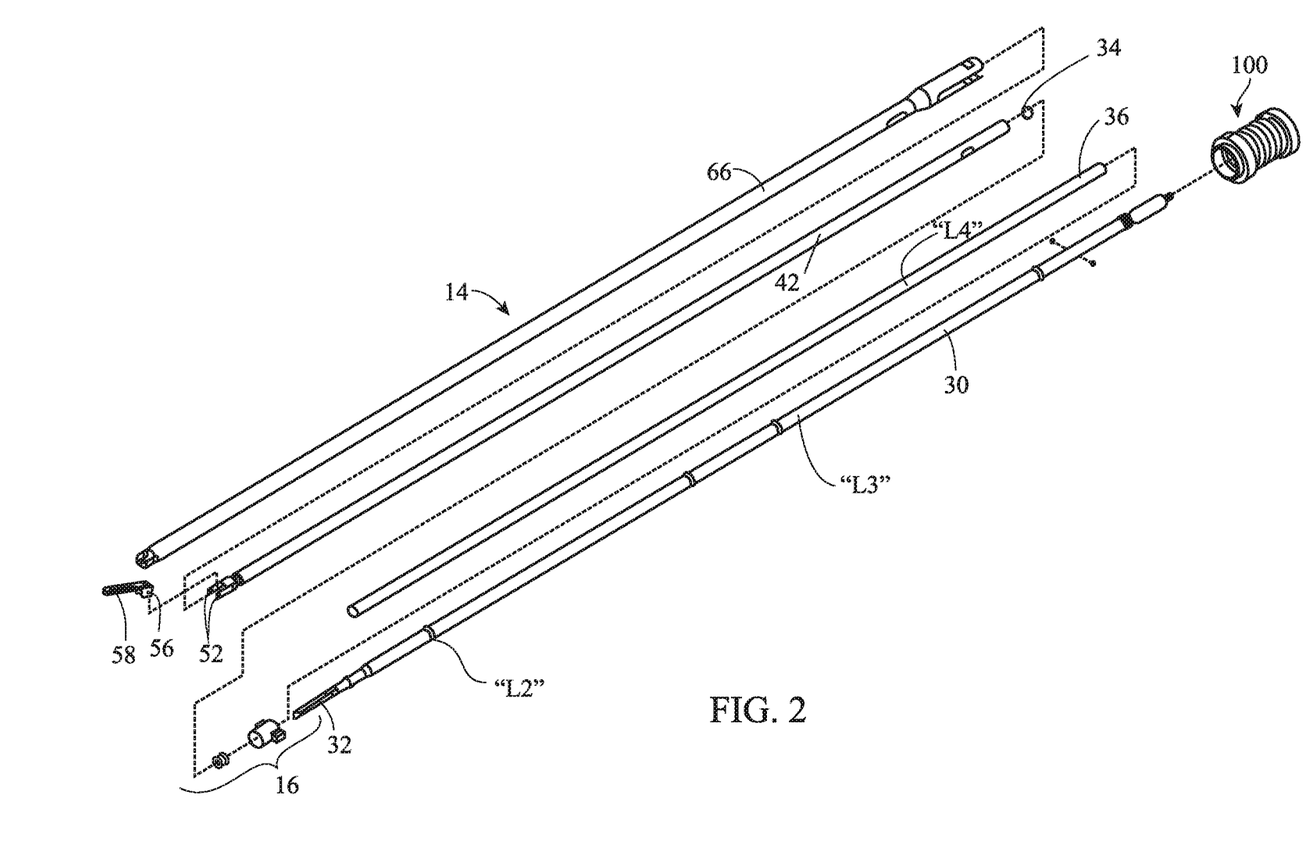
FIG. 2 is an exploded, perspective view of the shaft, waveguide, and tool assemblies of the ultrasonic surgical instrument of FIG. 1.
Figure 3:
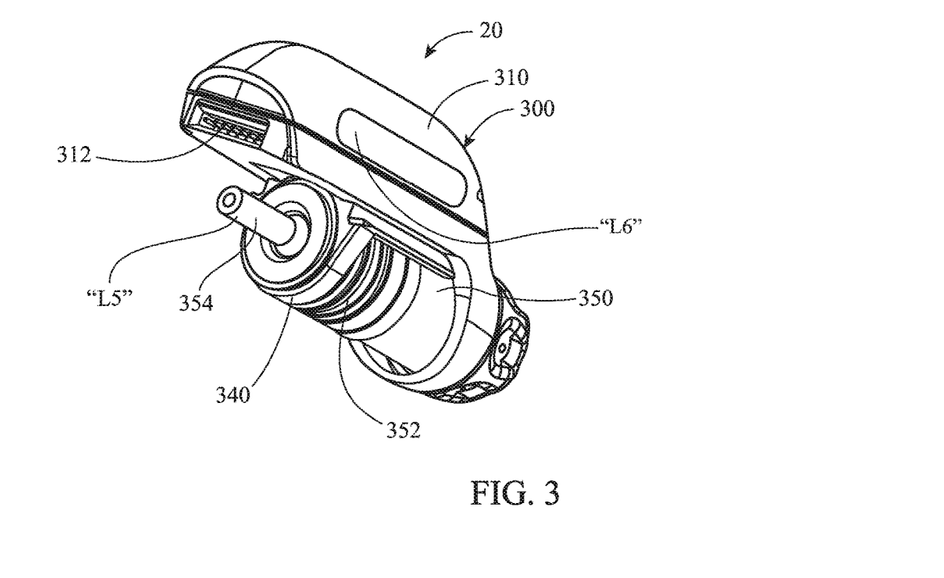
FIG. 3 is a side, perspective view of the ultrasonic transducer and generator assembly ("TAG") of the ultrasonic surgical instrument of FIG. 1.

Referring generally to FIGS. 1-3, the present disclosure provides ultrasonic surgical instruments and methods for sealing and/or cutting tissue. More specifically, the ultrasonic surgical instruments and methods of the present disclosure are configured to adjust the ultrasonic energy output, e.g., the displacement of the ultrasonic blade, based upon the tension on tissue, to facilitate sealing of tissue or cutting of tissue. An ultrasonic surgical instrument exemplifying the aspects and features of the present disclosure is shown generally identified by reference numeral 10. For the purposes herein, ultrasonic surgical instrument 10 is generally described. Aspects and features of ultrasonic surgical instrument 10 not germane to the understanding of the present disclosure are omitted to avoid obscuring such aspects and features of the present disclosure in unnecessary detail. Further, the aspects and features of the present disclosure are equally applicable for use with any other suitable ultrasonic surgical instrument.

Ultrasonic surgical instrument 10 generally includes a handle assembly 12, an elongated body 14 extending distally from handle assembly 12, and a tool assembly 16 disposed at a distal end portion of elongated body 14 and including a blade 32 and a clamp member 58. Handle assembly 12 supports a battery assembly 18 and an ultrasonic transducer and generator assembly ("TAG") 20, and includes a rotatable nozzle 22, an activation button 24, and a clamp trigger 26. Battery assembly 18 and TAG 20 are each releasably secured to handle assembly 12, and are removable therefrom to facilitate disposal of the entire device, with the exception of battery assembly 18 and TAG 20. However, it is contemplated that any or all of the components of ultrasonic surgical instrument 10 be configured as disposable single-use components or sterilizable multi-use components.

With reference to FIG. 2, elongated body 14 of ultrasonic surgical instrument 10 includes a waveguide 30 which extends distally from handle assembly 12 to tool assembly 16. A distal end portion of waveguide 30 defines blade 32 of tool assembly 16. A proximal end portion of waveguide 30 is configured to engage TAG 20 (FIGS. 1 and 3), as detailed below. An isolation tube 36 is positioned about waveguide 30 to prevent the transfer of ultrasonic energy from waveguide 30 to an inner support tube 42. One or more seal rings 34 is disposed about waveguide 30 to maintain spacing between waveguide 30 and isolation tube 36 while inhibiting fluid passage therebetween. Seal ring(s) 34 may be disposed at a node point(s) along waveguide 30 or in another suitable position(s). Waveguide 30 and inner support tube 42 are rotatably coupled to rotatable nozzle 22 (FIG. 1) such that rotation of nozzle 22 (FIG. 1) effects corresponding rotation of inner support tube 42 and waveguide 30. An actuator tube 66 which, as detailed below, is coupled to inner support tube 42, is similarly rotated upon rotation of nozzle 22 (FIG. 1).

Inner support tube 42 is positioned about isolation tube 36 and includes a distal end portion having a pair of spaced clamp support arms 52. Spaced clamp support arms 52 are configured to pivotally engage pivot members 56 (only one of which is visible in FIG. 2) formed on clamp jaw 58 of tool assembly 16 to enable pivoting of clamp jaw 58 between an open position, wherein clamp jaw 58 is spaced from blade 32, and a closed position, wherein clamp jaw 58 is approximated relative to blade 32. Clamp jaw 58 is moved between the open and closed positions in response to actuation of clamp trigger 26 (FIG. 1).

Outer actuator tube 66 is slidably supported about inner support tube 42 and is operably coupled to clamp jaw 58 such that, as actuator tube 66 is slid about inner support tube 42 between an advanced position and a retracted position, clamp jaw 58 is pivoted from the open position to the closed position. A proximal end of outer actuator tube 66 is operably coupled with rotatable nozzle 22 (FIG. 1) such that outer actuator tube 66 is rotatably secured to but slidable relative to rotatable nozzle 22 (FIG. 1). The proximal end of outer actuator tube 66 is also operably coupled with a drive mechanism 100.

Referring also to FIG. 1, drive mechanism 100 is supported within and configured for linear movement relative to handle assembly 12. Handle assembly 12 also includes the aforementioned clamp trigger 26, which is operably coupled with drive mechanism 100 such that, in use, when clamping trigger 26 is compressed towards battery assembly 18, drive mechanism 100 is moved to thereby move outer actuator tube 66 from the advanced position to the retracted position to pivot clamp jaw 58 from the open position to the closed position in relation to blade 32. Drive mechanism 100 is further configured to limit the application of clamping force to tissue grasped between clamp jaw 58 and blade 32. A spring (not explicitly shown) may be provided to bias clamping trigger 26 towards the initial position and, thus, clamp jaw 58 towards the open position.

Activation button 24 is supported on handle assembly 12. When activation button 24 is activated in an appropriate manner, an underlying switch assembly 170 is activated to effect communication between battery assembly 18 and TAG 20. As detailed below, switch assembly 170 may be configured as a two operational mode switch assembly 170 enabling activation from an "OFF" condition to either a "CUT" mode of operation or a "SEAL" mode of operation, depending upon the manner in which activation button 24 is activated (see FIGS. 4A-4B). Alternatively, as also detailed below, a switch assembly 1070 may be provided that enables activation from an "OFF" condition to an "ON" condition in response to appropriate activation of activation button 24 (see FIGS. 5A-5B) or from an "OFF" condition to either a "LOW" power mode of operation or a "HIGH" power mode of operation.

Figure 4A:
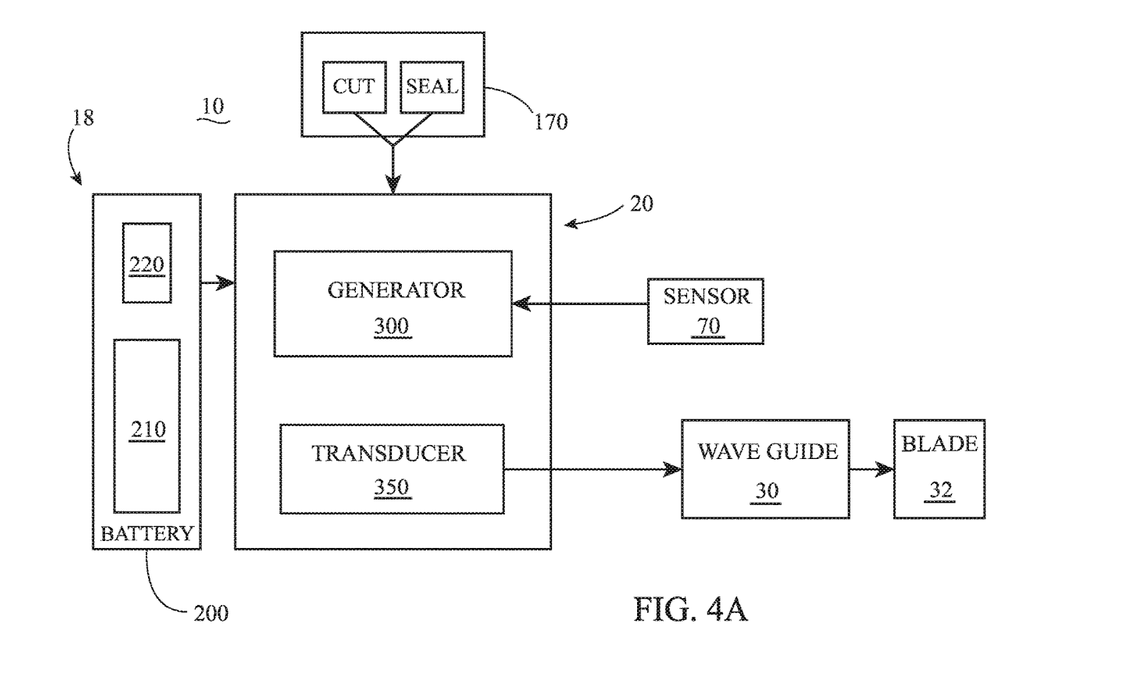
FIG. 4A is a schematic illustration of the ultrasonic surgical instrument of FIG. 1.

Continuing with reference to FIGS. 1 and 2, battery assembly 18 is connected to a lower end of handle assembly 12 to define a fixed handgrip portion of handle assembly 12 and includes an outer housing 200 that houses one or more battery cells 210 and a microcontroller 220 including a processor and a memory (see FIG. 4A). A series of contacts (not explicitly shown) disposed on outer housing 200 enable communication of power and/or control signals between the internal components of battery assembly 18, switch assembly 170 (FIG. 4A), and TAG 20, although contactless communication therebetween is also contemplated.

With additional reference to FIG. 3, TAG 20 includes a generator 300 and an ultrasonic transducer 350. Generator 300 includes an outer housing 310 that houses the internal operating components thereof, e.g., drive signal generating circuitry, a microcontroller, and a memory (not explicitly shown). TAG 20 further includes one or more support members 340 extending from outer housing 310 of generator 300 that define one or more cradles for rotatably supporting ultrasonic transducer 350. Ultrasonic transducer 350 includes a piezoelectric stack 352 and a forwardly extending horn 354. Horn 354 is configured to threadably engage the proximal end of waveguide 30 (FIG. 2), although other suitable engagement mechanisms are also contemplated. A series of contacts 312 associated with TAG 20 enable communication of power and/or control signals between TAG 20, battery assembly 18, and switch assembly 170 (FIG. 4A), although contactless communication therebetween is also contemplated.

In general, in use, when battery assembly 18 and TAG 20 are attached to handle assembly 12 and waveguide 30 and ultrasonic surgical instrument 10 is activated, e.g., upon activation of activation button 24, switch assembly 170 (FIG. 4A) signals battery cells 210 (FIG. 4A) to provide power to generator 300 of TAG 20 which, in turn, uses this power to provide a drive signal to ultrasonic transducer 350 of TAG 20. Ultrasonic transducer 350, in turn, converts the drive signal into high frequency mechanical motion. This high frequency mechanical motion produced by ultrasonic transducer 350 is transmitted to blade 32 via waveguide 30 such that blade 32 oscillates within the ultrasonic frequency range. In this manner, blade 32 may be utilized to treat, e.g., seal and/or cut, tissue adjacent to blade 32 or clamped between blade 32 and clamp jaw 58.

Referring to FIG. 4A, the power provided from battery cells 210 to generator 300 effects the drive signal provided from generator 300 to ultrasonic transducer 350 which, in turn, effects the mechanical motion produced by ultrasonic transducer 350 and, thus, the displacement of blade 32 as blade 32 oscillates within the ultrasonic frequency range. As such, the power provided from battery cells 210 to generator 300 may be varied to vary the drive signal provided from generator 300 to ultrasonic transducer 350, thereby varying the displacement of blade 32, although other suitable controls for varying the drive signal and, thus, the displacement of blade 32 are also contemplated.

Different displacements of blade 32 affect tissue in different manners. For example, a greater displacement of blade 32 results in relatively faster tissue cutting and relatively less tissue sealing, while a smaller displacement of blade 32 results in relatively less tissue cutting and relatively better tissue sealing. Accordingly, where tissue cutting is desired, a greater displacement of blade 32 is utilized. Where tissue sealing is desired, a lesser displacement of blade 32 is utilized.

Differences in tension on tissue, e.g., tension applied by blade 32 and/or clamp jaw 58 (FIGS. 1 and 2), also result in different tissue effects. For example, applying ultrasonic energy from blade 32 to tissue under greater tension results in relatively faster tissue cutting and relatively less tissue sealing, while applying ultrasonic energy from blade 32 to tissue under less tension results in relatively less tissue cutting and relatively better tissue sealing.

Since both displacement of blade 32 and tension on tissue effect whether relatively faster tissue cutting is achieved or relatively better tissue sealing is achieved, the displacement of blade 32 can be varied based upon the tension on tissue to achieve a desired result, e.g., faster tissue cutting or better tissue sealing. To this end, ultrasonic surgical instrument 10 is provided with one or more sensors 70 (FIG. 4A) configured to sense a force that correlates to a relative amount of tension on tissue. Sensor 70, in turn, is coupled to the microcontroller (not shown) of generator 300 and/or microcontroller 220 of battery assembly 18 to enable the drive signal provided from generator 300 to ultrasonic transducer 350 to be adjusted based upon whether or not, or the extent to which, there is tension on tissue, as detailed below.

Sensor 70, more specifically, operates to sense, directly or indirectly, a relative amount of force acting on blade 32, which is indicative of the tension on tissue, e.g., whether blade 32 is applying greater force to tissue such that tissue is relatively more tensioned or whether blade 32 is applying less force to tissue such that tissue is relatively less tensioned. Sensor 70 may take various forms and/or may be disposed at various positions on ultrasonic surgical instrument 10 (FIG. 1). Exemplary sensors 70 and positions of sensor 70 on ultrasonic surgical instrument 10 (FIG. 1) are detailed below; however, any suitable sensor 70 in any suitable position may be utilized in accordance with the present disclosure.

Sensor 70 may be configured as a strain gauge or other suitable progressive sensor configured to sense a relative degree of force across a range. Alternatively, sensor 70 may be configured as a contact (ON/OFF) sensor or other suitable sensor configured to sense whether a force exceeds a threshold force.

In embodiments, with reference to FIGS. 1 and 4A, sensor 70 may be disposed, for example, at location "L1" at the junction between the fixed handle portion of handle assembly 12 and the body portion of handle assembly 12, since force applied by a user to handle assembly 12 at "L1" to urge blade 32 into tissue to tension tissue is indicative of the tension on tissue.

Referring to FIGS. 2 and 4A, sensor 70, in embodiments, may be disposed at location "L2" or "L3" on waveguide 30, since force applied by blade 32 to tissue will result in a torque applied to waveguide 30 that is indicative of the tension on tissue. Locations "L2" and "L3" may be at nodes of waveguide 30, e.g., adjacent to the one or more seal rings 34 disposed about waveguide 30, or at other suitable positions along waveguide 30. At locations "L2" and "L3" on waveguide 30, sensor 70 may be configured as a strain gauge printed directly onto waveguide 30 or may be any other suitable sensor coupled to waveguide 30 in any other suitable manner.

Continuing with reference to FIGS. 2 and 4A, in embodiments, sensor 70 may be disposed at location "L4" on the interior of isolation tube 36, since force applied by blade 32 to tissue will result in a torque applied to waveguide 30 which, in turn, will result in a force on isolation tube 36 (from direct contact with waveguide 30 or indirectly via contact of component(s) therebetween) that is indicative of the tension on tissue. To this end, waveguide 30 may include an outwardly-extending protrusion (not explicitly shown) and/or sensor 70 may protrude inwardly from isolation tube 36 to facilitate contact between waveguide 30 and sensor 70. Alternatively, sensor 70 may be positioned adjacent one or more of the seal rings 34 disposed about waveguide 30 between waveguide 30 and isolation tube 36. Instead of being disposed at location "L4," sensor 70 may alternatively be disposed at any suitable position on isolation tube 36.

Turning to FIGS. 3 and 4A, sensor 70 may be disposed at location "L5," on horn 354 of transducer 350 of TAG 20. Similarly as with waveguide 30 (FIG. 2), the force applied by blade 32 to tissue will result in a torque applied to horn 354 that is indicative of the tension on tissue.

In embodiments, sensor 70 is disposed at location "L6" and is configured as an impedance sensor configured to sense the impedance of transducer 350. With a plurality of readings of the impedance of transducer 350 from sensor 70 over time, the resultant impedance curve can be analyzed to determine whether blade 32 is putting tension (or relatively more tension) on tissue or if blade 32 is not putting tension (or relatively less tension) on tissue, thus indicating the tension on tissue. More specifically, if the change in impedance over time is above a threshold, sensor 70 may indicate that there is tension (or relatively more tension) on tissue. On the other hand, if the change in impedance is below the threshold, sensor 70 may indicate that there is no tension (or relatively less tension) on tissue. Other suitable impedance to tissue tension correlations are also contemplated. Other suitable sensors configured to determine tension on tissue based upon electrical characteristics of transducer 350, battery assembly 18, and/or generator 300 are also contemplated.

Referring to FIG. 4A, as detailed above, sensor 70 is coupled to the microcontroller (not shown) of generator 300 and/or microcontroller 220 of battery assembly 18 to enable the drive signal provided from generator 300 to ultrasonic transducer 350 to be adjusted, to thereby adjust the displacement of blade 32. More specifically, displacement of blade 32 is adjusted, e.g., increased, decreased, or maintained, based upon whether tension on tissue (or tension on tissue above a threshold) is detected, as indicated by sensor 70, and based upon the operating mode of ultrasonic surgical instrument 10, as indicated by switch assembly 170, to facilitate treatment of tissue in the manner desired.

Activation button 24 of handle assembly 12 (see FIG. 1), as noted above, is selectively activatable by a user in a first activated position or a second activated position to activate underlying switch assembly 170 in a "CUT" mode of operation or a "SEAL" mode of operation, respectively. Switch assembly 170 communicates with the microcontroller (not shown) of generator 300 and/or microcontroller 220 of battery assembly 18 to indicate whether the user has activated activation button 24 (FIG. 1) in the first activated position, corresponding to the "CUT" mode of operation, or in the second activated position, corresponding to the "SEAL" mode of operation.

Figure 4B:
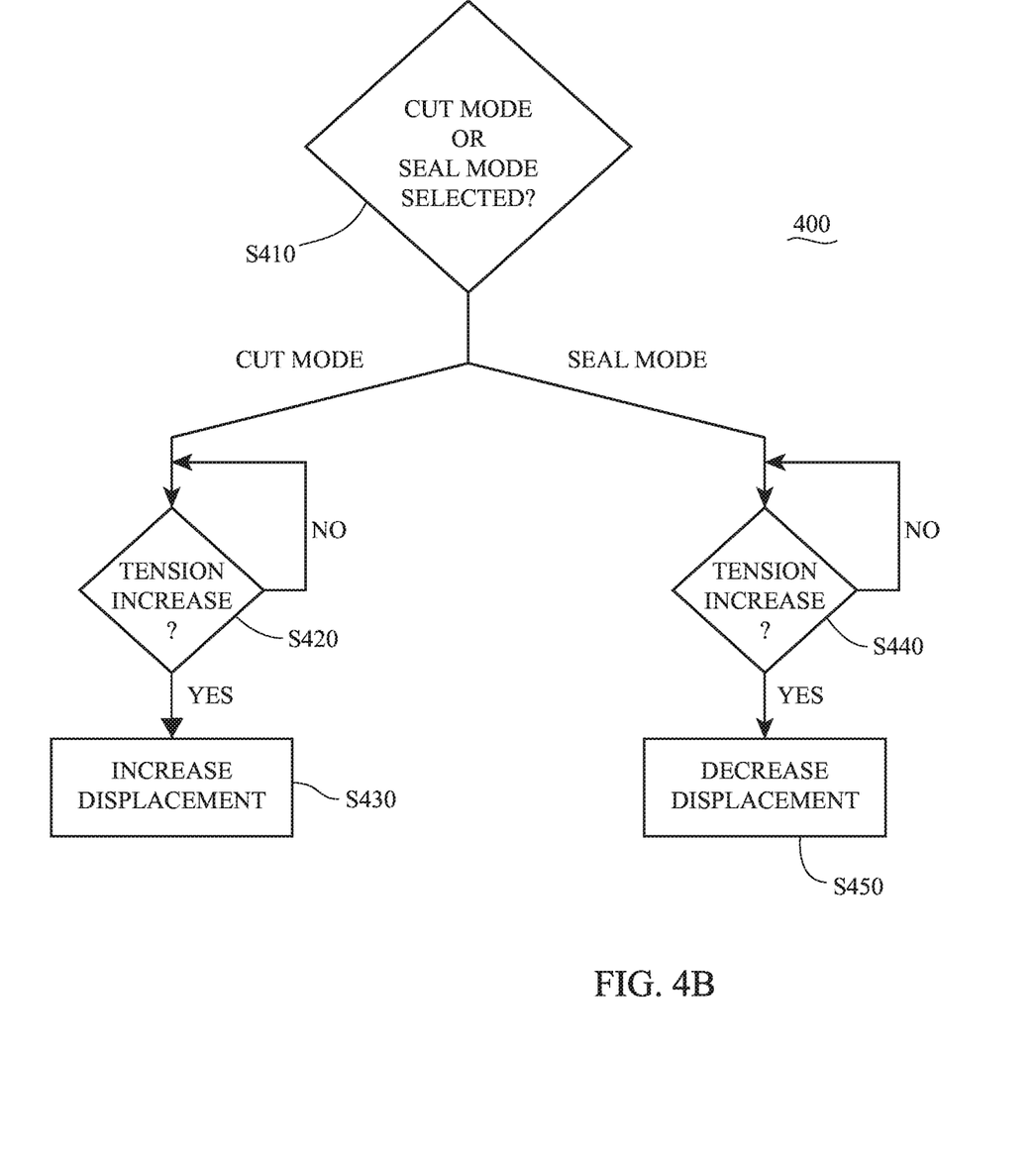
FIG. 4B is a flow diagram illustrating a method of using an ultrasonic surgical instrument provided in accordance with aspects of the present disclosure.

With additional reference to FIG. 4B, the use of ultrasonic surgical instrument 10 according to method 400 is detailed. Initially, as indicated at S410, the microcontroller (not shown) of generator 300 and/or microcontroller 220 of battery assembly 18 determines, based upon the information received from switch assembly 170, whether switch assembly 170 has been activated in the "CUT" mode of operation or the "SEAL" mode of operation.

If it is determined at S410 that ultrasonic surgical instrument 10 is operating in the "CUT" mode of operation ("CUT MODE" in S410), the method proceeds to S420. In a default condition in the "CUT" mode of operation, blade 32 is oscillating with a relatively high displacement, as a relatively high displacement facilitates faster tissue cutting and relatively less tissue sealing. However, even with blade 32 oscillating with the relatively high displacement, some tissue sealing may still be effected. Thus, in order to further facilitate tissue cutting in the "CUT" mode of operation, it is determined, at S420, whether tension on tissue has increased, or has increased above a threshold. More specifically, the microcontroller (not shown) of generator 300 and/or microcontroller 220 of battery assembly 18 may determine whether tension on tissue has increased or has increased above a threshold based upon feedback received from sensor 70, as detailed above.

If it is determined that tension on tissue has increased or increased above a threshold ("YES" at S420), the microcontroller (not shown) of generator 300 and/or microcontroller 220 of battery assembly 18 adjusts the drive signal provided from generator 300 to ultrasonic transducer 350 to thereby increase the displacement of blade 32 from the default relatively high displacement to a higher displacement, as indicated at S430. Such a feature enables even faster tissue cutting and even less tissue sealing (as a result of the higher displacement of blade 32), in response to more tension on tissue, which is indicative of the user urging blade 32 into tissue, a motion typically indicative of an intent to cut through the tissue.

If it is determined that tension on tissue has not increased ("NO" at S420), the relatively high displacement, corresponding to the default condition in the "CUT" mode of operation, is maintained. Further, sensor 70 may be continuously or periodically monitored, repeating S420, to continuously or periodically determine whether tension on tissue has increased.

Continuing with reference to FIGS. 4A and 4B, if it is determined at S410 that ultrasonic surgical instrument 10 is operating in the "SEAL" mode of operation ("SEAL MODE" in S410), the method proceeds to S440. In a default condition in the "SEAL" mode of operation, blade 32 is oscillating with a relatively low displacement, as a relatively low displacement facilitates better tissue sealing as compared to less tissue cutting. However, even with blade 32 oscillating with the relatively low displacement, some tissue cutting may still be effected. Thus, in order to further facilitate tissue sealing in the "SEAL" mode of operation, it is determined, at S440, whether tension on tissue has increased, or has increased above a threshold. More specifically, the microcontroller (not shown) of generator 300 and/or microcontroller 220 of battery assembly 18 may determine whether tension on tissue has increased or has increased above a threshold based upon feedback received from sensor 70, as detailed above. If it is determined that tension on tissue has increased or increased above a threshold ("YES" at S440), the microcontroller (not shown) of generator 300 and/or microcontroller 220 of battery assembly 18 adjusts the drive signal provided from generator 300 to ultrasonic transducer 350 to thereby decrease the displacement of blade 32 from the default relatively low displacement to a lower displacement, as indicated at S450.

A lower displacement enables better tissue sealing and less tissue cutting and, thus, serves to counteract the effect of increased tension on tissue, which tends to result in faster tissue cutting. Accordingly, the displacement of blade 32 is lowered in such instances to achieve the user-intended result, tissue sealing, since ultrasonic surgical instrument 10 is operating in the "SEAL" mode.

If it is determined that tension on tissue has not increased ("NO" at S440), the relatively low displacement, corresponding to the default condition in the "SEAL" mode of operation, is maintained. Further, sensor 70 may be continuously or periodically monitored, repeating S440, to continuously or periodically determine whether tension on tissue has increased.

Figure 5A:
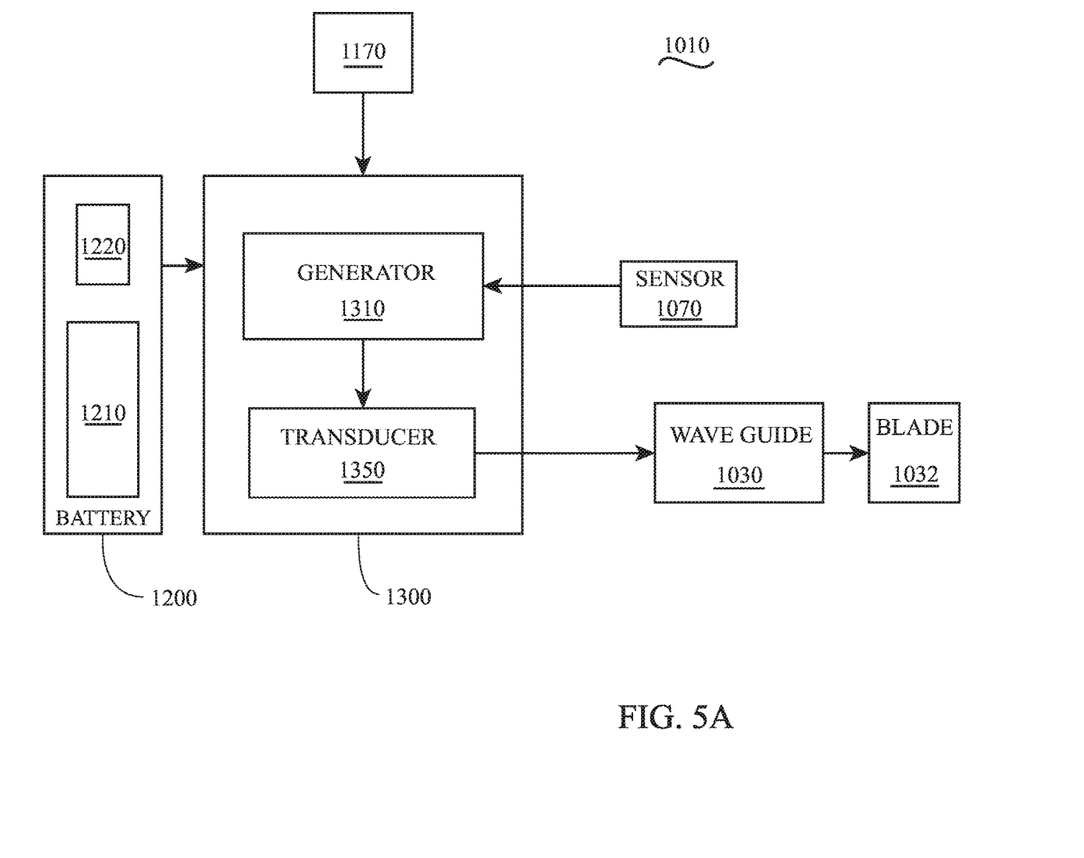
FIG. 5A is a schematic illustration of another ultrasonic surgical instrument provided in accordance with aspects of the present disclosure.
Figure 5B:
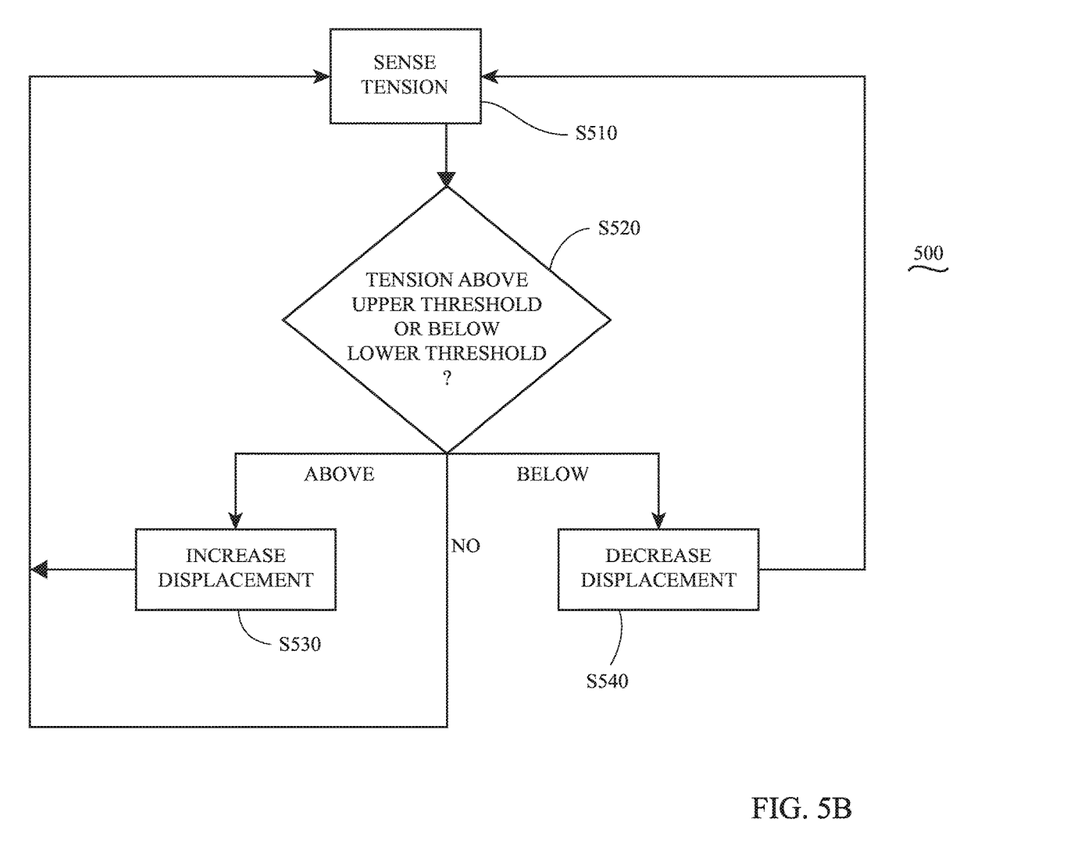
FIG. 5B is a flow diagram illustrating another method of using an ultrasonic surgical instrument provided in accordance with aspects of the present disclosure.

Turning to FIGS. 5A-5B, another embodiment of an ultrasonic surgical instrument 1010 and method of use 500 provided in accordance with the present disclosure are described. Ultrasonic surgical instrument 1010 is similar to and may include any of the features of ultrasonic surgical instrument 10 (FIG. 1), except as specifically contradicted below. Accordingly, similar features will be summarily described below or omitted entirely.

Ultrasonic surgical instrument 1010 includes a handle assembly (not explicitly shown), an elongated assembly including a waveguide 1030 having a blade 1032 extending distally therefrom, and a battery assembly 1200 and TAG 1300, each of which is configured for releasable mounting on the handle assembly. Ultrasonic surgical instrument 1010 further includes a sensor 1070 and a switch assembly 1170 associated with an activation button (not shown). The activation button is selectively actuatable to activate switch assembly 1170 from an "OFF" condition to an "ON" condition. When activated to the "ON" condition, switch assembly 1170 communicates with the microcontroller (not shown) of generator 1310 and/or microcontroller 1220 of battery assembly 1200 to indicate that the activation button has been actuated.

The use of ultrasonic surgical instrument 1010 according to method 500 is detailed. Initially, ultrasonic surgical instrument 1010 is activated to operate in a default condition, wherein the microcontroller (not shown) of generator 1310 and/or microcontroller 1220 of battery assembly 1200 direct the application of an appropriate power from battery cells 1210 to generator 1310 to achieve an appropriate drive signal from generator 1310 to ultrasonic transducer 1350 to thereby transmit ultrasonic energy along waveguide 1030 to blade 1032 to oscillate blade 1032 at a default displacement.

At S510, the tension on tissue is sensed using sensor 1070. The tension on tissue may be sensed continuously or periodically. At S520, based upon the information received from sensor 1070, the microcontroller (not shown) of generator 1310 and/or microcontroller 1220 of battery assembly 1200 determines whether the tension on tissue is above an upper threshold or below a lower threshold.

If it is determined that the tension on tissue is above the upper threshold ("ABOVE" at S520), the method proceeds to S530, wherein the microcontroller (not shown) of generator 1310 and/or microcontroller 1220 of battery assembly 1200 adjusts the drive signal provided from generator 1310 to ultrasonic transducer 1350 to thereby increase the displacement of blade 1032 from the default displacement to a higher displacement, as indicated at S530. Such a feature enables faster tissue cutting and less tissue sealing (as a result of the higher displacement of blade 1032), in response to more tension on tissue, which is indicative of the user urging blade 1032 into tissue, a motion typically indicative of an intent to cut through the tissue.

If it is determined that the tension on tissue is below the lower threshold ("BELOW" at S520), the method proceeds to S540, wherein the microcontroller (not shown) of generator 1310 and/or microcontroller 1220 of battery assembly 1200 adjusts the drive signal provided from generator 1310 to ultrasonic transducer 1350 to thereby decrease the displacement of blade 1032 from the default displacement to a lower displacement, as indicated at S530. Such a feature enables better tissue sealing and less tissue cutting (as a result of the lower displacement of blade 1032), in response to less tension on tissue, which is indicative of an intent to seal tissue.

If it is determined that the tension on tissue is neither above the upper threshold nor below the lower threshold ("NO" at S520), e.g., where the tension on tissue is between the upper and lower thresholds, the displacement of blade 1032 is maintained at the default displacement. Method 500 may be repeated continuously or periodically to adjust the displacement of blade 1032 according to the tension on tissue continuously or periodically, as detailed above.

As an alternative to the activation button of ultrasonic surgical instrument 1010 selectively actuatable to activate switch assembly 1170 from an "OFF" condition to an "ON" condition, the activation button may alternatively be configured to selectively activate switch assembly 1170 from an "OFF" condition to a "LOW" power mode of operation or a "HIGH" power mode of operation, depending upon the manner in which the activation button is actuated. In such configurations, method 500 would proceed similarly as above except that a "LOW" default displacement is provided in the "LOW" power mode of operation and a higher, "HIGH" default displacement is provided in the "HIGH" power mode of operation (the upper and lower thresholds for each of the modes may also be different).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical system, comprising:
   an ultrasonic generator configured to output a drive signal;
   an ultrasonic transducer coupled to the ultrasonic generator and configured to receive the drive signal and output mechanical motion in response thereto;
   a waveguide coupled to the ultrasonic transducer and configured to transmit the mechanical motion therealong;
   a blade disposed at a distal end portion of the waveguide, the blade configured to oscillate in response to receipt of the mechanical motion from the waveguide, wherein the blade defines a displacement when oscillating;
   a sensor configured to sense a property indicative of tension on tissue; and
   a controller configured to adjust the drive signal to thereby adjust the displacement based upon the sensed property.

2. The ultrasonic surgical system according to claim 1, wherein the sensor is configured to sense a force on the waveguide.

3. The ultrasonic surgical system according to claim 1, wherein the sensor is configured to sense an impedance of the ultrasonic transducer.

4. The ultrasonic surgical system according to claim 1, wherein, if the sensed property indicates tension on tissue is increased above a threshold, the controller is configured to adjust the drive signal to increase the displacement of the blade.

5. The ultrasonic surgical system according to claim 1, wherein, if the sensed property indicates tension on tissue is decreased below a threshold, the controller is configured to adjust the drive signal to decrease the displacement of the blade.

6. The ultrasonic surgical system according to claim 1, further comprising an activation switch operably coupled to the ultrasonic generator, the activation switch selectively activatable in a "CUT" mode and a "SEAL" mode.

7. The ultrasonic surgical system according to claim 6, wherein, when the activation switch is activated in the "SEAL" mode, if the sensed property indicates tension on tissue is increased, the controller is configured to adjust the drive signal to decrease the displacement of the blade.

8. The ultrasonic surgical system according to claim 6, wherein, when the activation switch is activated in the "CUT" mode, if the sensed property indicates tension on tissue is increased, the controller is configured to adjust the drive signal to increase the displacement of the blade.

9. The ultrasonic surgical system according to claim 1, further comprising a handle assembly supporting the ultrasonic transducer thereon, wherein the waveguide extends distally from the handle assembly.

10. The ultrasonic surgical system according to claim 9, wherein the handle assembly further supports the ultrasonic generator and a battery assembly thereon, the battery assembly configured to power the ultrasonic generator to produce the drive signal.

11. The ultrasonic surgical system according to claim 10, wherein the controller controls an amount of power delivered from the battery assembly to the ultrasonic generator to thereby adjust the drive signal.

12. A method of treating tissue, comprising:
applying a drive signal to an ultrasonic transducer to oscillate an ultrasonic blade adjacent tissue, the oscillating ultrasonic blade defining a displacement;
sensing a property indicative of a tension on the tissue; and
adjusting the drive signal applied to the ultrasonic transducer based upon the sensed property to thereby adjust the displacement.

13. The method according to claim 12, wherein sensing the property includes sensing a force on a waveguide coupled to the ultrasonic blade.

14. The method according to claim 12, wherein sensing the property includes sensing an impedance of the ultrasonic transducer.

15. The method according to claim 12, wherein, if the sensed property indicates tension on tissue is increased above a threshold, the drive signal is adjusted to increase the displacement of the blade.

16. The method according to claim 12, wherein, if the sensed property indicates tension on tissue is decreased below a threshold, the drive signal is adjusted to decrease the displacement of the blade.

17. The method according to claim 12, further comprising:
determining whether a "CUT" mode of operation or a "SEAL" mode of operation is selected; and
adjusting the drive signal applied to the ultrasonic transducer based upon the sensed property and the selected mode of operation to thereby adjust the displacement.

18. The method according to claim 17, wherein, in the "SEAL" mode of operation, if the sensed property indicates tension on tissue is increased, the drive signal is adjusted to decrease the displacement of the blade.

19. The method according to claim 17, wherein, in the "CUT" mode, if the sensed property indicates tension on tissue is increased, the drive signal is adjusted to increase the displacement of the blade.

20. The method according to claim 12, wherein adjusting the drive signal includes adjusting an amount of power delivered from a power source to an ultrasonic generator configured to output the drive signal.

* * * * *